United States Patent [19]

Narula et al.

[11] Patent Number: 5,236,897
[45] Date of Patent: Aug. 17, 1993

[54] PERFUMERY USE OF 2,2-DIMETHYL-4(2' OR 4' PYRIDYL) BUTYRONITRILE AND PROCESS FOR PREPARING SAME

[75] Inventors: Anubhav P. S. Narula, Hazlet; John J. De Virgilio, Red Bank; William L. Schreiber, Freehold, all of N.J.

[73] Assignee: International Flavors & Fragrances Inc., New York, N.Y.

[21] Appl. No.: 1,952

[22] Filed: Jan. 8, 1993

Related U.S. Application Data

[60] Continuation-in-part of Ser. No. 858,536, Mar. 27, 1992, Pat. No. 5,179,222, which is a division of Ser. No. 759,155, Sep. 13, 1991, Pat. No. 5,143,899.

[51] Int. Cl.$^5$ ................................................ A61K 7/46
[52] U.S. Cl. .................... 512/6; 252/174.11; 252/187.25
[58] Field of Search ............. 512/6; 252/174.11, 187.25

[56] References Cited

U.S. PATENT DOCUMENTS

| | | | |
|---|---|---|---|
| 5,143,899 | 9/1992 | Narula et al. ............................. | 512/6 |
| 5,179,227 | 1/1993 | Narula et al. ............................. | 512/6 |

OTHER PUBLICATIONS

Magnus, et al, Chemical Abstracts vol. 51, columns 3595 and 3596 (beginning at 3595g) (abstract of J. Am. Chem. Soc. 78, pp. 4127-4130 (1956).

*Primary Examiner*—James H. Reamer
*Attorney, Agent, or Firm*—Arthur L. Liberman

[57] ABSTRACT

Described are the 2,2-dimethyl-4(2' or 4'-pyridyl) butyronitriles defined according to the generic structure:

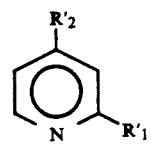

wherein one of $R_1'$ or $R_2'$ is the moiety:

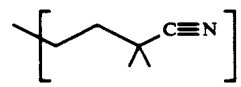

and the other of $R_1'$ or $R_2'$ is hydrogen as well as perfumery uses thereof and processes for preparing same.

7 Claims, 7 Drawing Sheets

GC SPECTRUM FOR EXAMPLE I.

G C PROFILE FOR EXAMPLE II.

FIG.5 NMR SPECTRUM FOR EXAMPLE II.

IR SPECTRUM FOR EXAMPLE II.

PERFUMERY USE OF 2,2-DIMETHYL-4(2' OR 4' PYRIDYL) BUTYRONITRILE AND PROCESS FOR PREPARING SAME

This application is a continuation-in-part of application for U.S. Pat. Ser. No. 858,536 filed on Mar. 27, 1992, U.S. Pat. No. 5,179,222 which is a divisional of application for U.S. Pat. Ser. No. 759,155 filed on Sep. 13, 1991, now U.S. Pat. No. 5,143,899 issued on Sep. 1, 1992.

BACKGROUND OF THE INVENTION

This invention relates to 2,2-dimethyl-4(2' or 4'-pyridyl) butyronitriles, methods of preparing same and uses thereof in augmenting, imparting or enhancing aromas in or to perfume compositions, perfumed articles and/or colognes.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting substantive green, new mown hey, fresh lilac, minty and herbaceous aromas with minty and new mown hey undertones are highly desirable in several types of perfume compositions, perfumed articles and colognes (e.g., piney fragrances).

The perfume uses of nitrile-contraining derivatives are well known in the prior art. Thus, the compound having the structure:

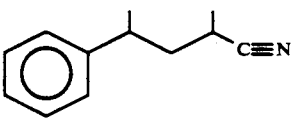

is shown to be useful in perfumery in U.S. Pat. No. 4,837,351 issued on Jun. 6, 1989 wherein it is indicated that it has a powerful fresh, fruity, floral odor note accompanied by a citrus, green topnote. Furthermore, U.S. Pat. No. 3,325,369 discloses the use of cinnamonitrile as a material useful in augmenting or enhancing the aroma of perfume compositions.

Other nitriles containing gem-dimethyl moieties "alpha" to the cyanide moiety are disclosed in Blumenthal, et al, U.S. Pat. No. 3,168,550 issued on Feb. 2, 1965.

Nothing in the prior art discloses the use in perfumery of the 2,2-dimethyl-4(2' or 4'-pyridyl) butyronitriles of our invention.

The preparation of phenyl butyronitriles are taught in the prior art to be rather complex and costly. Thus, 2,2-dimethyl-4-phenyl valeronitrile is shown to be prepared according to the reaction:

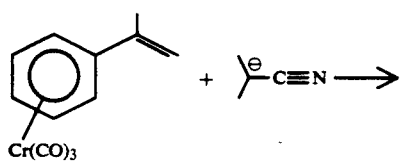

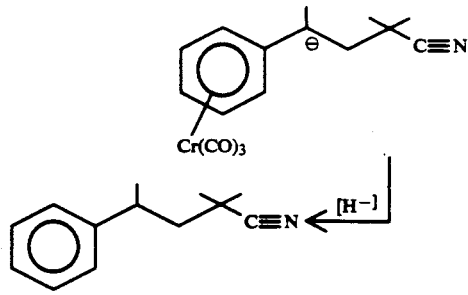

using a chromium carbonyl complex by Semmelhack, et al, J. Am. Chem. Soc., 1980, 102, 6584–6586.

The preparation of 2,2-dimethyl-4-phenyl(2' pyridyl) butyronitrile having the structure:

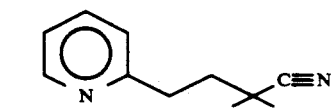

is disclosed in Magnus, et al, J. Am. Chem. Soc., Volume 78, (1956) at pages 4127 and 4130. The reaction shown thereat is:

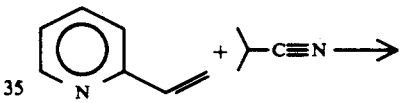

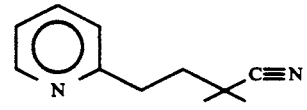

using a sodium metal catalyst (and not the catalyst disclosed and claimed in the instant application). The Magnus, et al reference is abstracted at Chem.Abstract, Volume 51, column 3595 g. Magnus, et al also discloses the reactions:

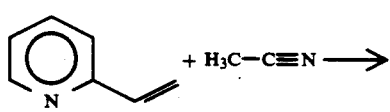

and

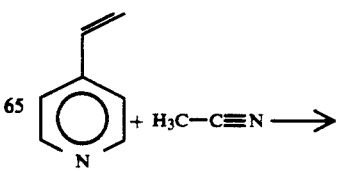

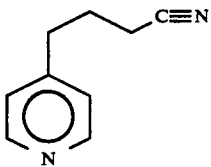

to produce, respectively the compounds having the structures:

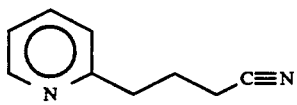

and

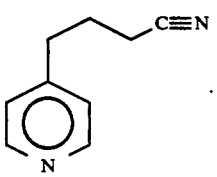

Nothing in the prior art discloses the use of sodium hydride or lithium diisopropyl amide having the structure:

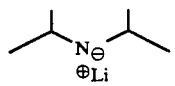

as a catalyst for carrying out the reactions:

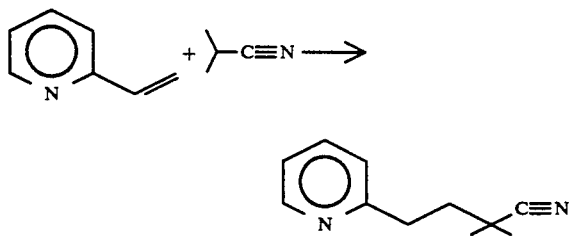

and

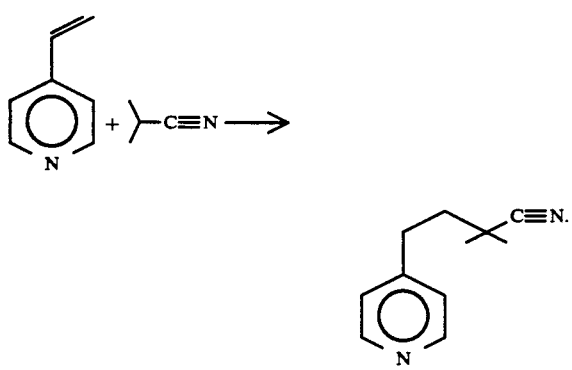

Furthermore, considerable difficulties have heretofore been encountered in using compounded hypochlorite bleach or sterilizing solutions with perfumed oils so that a stablelong-lasting, single phase commercially feasible bleach or sterilizing solution has been difficult to obtain, particularly wherein the desired aroma of the article bleached or sterilized (e.g., clothing) has a pleasant and stable and consistent aroma on drying (and not the usual "hypochlorite-bleached-article" aroma). The problem has been defined in United Kingdom Patent Specification No. 886,084 published on Jan. 3, 1962 wherein it is stated that a stable "dispersion" of hypochlorite-resistant perfume in aqueous solutions of hypochlorites was formulated. United Kingdom Patent Specification No. 886,084 discloses the preparation of an aqueous solution of a hypochlorite containing a hypochlorite resistant perfume and a surface active quaterary ammonium compound of the betaine type soluble in the hypochlorite solution. Such ammonium compounds have the generic structure:

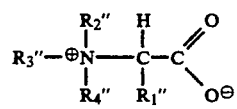

wherein each of $R_1$, $R_2$, $R_3$ and $R_4$ are alkyl. One of the features of the perfumed solution produced in accordance with said United Kingdom Patent Specification No. 886,084 is indicated to be that the solution exhibits foaming properties. Another feature of United Kingdom Patent Specification No. 886,084 is stated to be that the perfumed solutions covered by the patent are found to be clear and homogeneous after eight weeks of storage at room temperature. Nevertheless, betaines such as ":Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long-lasting stable soluble single phase thickened perfumed aqueous alkali metla hypochorite bleach or steriling solutions having the long-lasting pleasant stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochorite" aroma is substantially eliminated from aromas of the end product to which the bleach or sterilizing solution is applied; particularly on dry-out, as well as from the aroma of the hands of the user when they in direct contact with such bleach or sterilizing solutions.

U.S. Pat. No. 3,560,389 also discloses the feasibility of using perfume oils in hyposchlorite bleaches or sterilizers at column 3, lines 37-40 but the disclosure is limited to inclusion of various detergents in addition to amine oxides, such as lithium lauryl sulfate and sodium lauryl ether sulfate and/or is further limited to include hydrotropes such as socium xylene sulfonate in addition to the amine oxide. Exclusion of such hydrotropes and detergents additional to the amine oxides and diphenyl oxide derivatives of our invention is desirable not only to cause the phenyl butyronitriles of our invention to function properly but also from an ecological standpoint.

European Chemical News, Volume 13, Jan. 18, 1968, sets forth a synopsis of South African Patent No.

67/4667 which corresponde to U.S. Pat. No. 3,560,389, but the reference also states at page 42:

"Alternatively, a detergent with bleaching or bacteriocidal properties can be formulated. Perfuming bleaching solutions is not possible."

Neither the South African nor the United States Patents, however, indicate the advantages and usefulness of limiting the detergents either to (a) compounds having the generic structure:

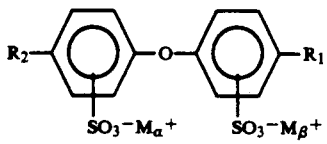

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other of $R_1$ or $R_2$ is pH-adjusted hydrogen and wherein $M_{60}$ and $M_{62}$ are the same or different and each represents alkyl metal which may be sodium, lithium or potassium, or (b) to mixtures of compounds having the structure:

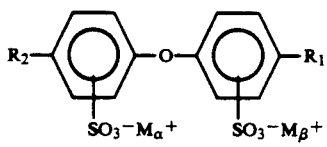

with at least one amine oxide defined according to the structure:

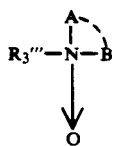

of excluding from the formulation a hydrotrope or of specifying the nature of the perfume oil useful in the perfumed bleach or sterilizing solution (wherein A and B are each separately methyl or taken together, complete a morpholino ring and wherein $R_3$ is straight chain alkyl having from 11 up to 13 carbon atoms).

U.S. Pat. No. 3,876,551 in attempting to solve the foregoing problem discloses a stable single phase aqueous alkyl metal hypochlorite liquid perfume bleach or sterilizing composition comprising an aqueous mixture of (1) an amine oxide composition consisting essentially of at least one morpholino and/or dimethyl ($C_{11}$–$C_{13}$ straight chain alkyl amine oxide in an amount greater than 55% of said amine oxide composition, (2) at least one alkali metal hydroxide, (3) at least one alkali metal hypochlorite, and (4) a perfume oil compatible with the mixture capable of imparting a "woody" or a "floral" or a "clean fresh" or a "citrusy" note to the bleach or sterilizing compositions; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above-named mixture comprising the steps of combining an amide oxide composition consisting essentially of one or more morpholino and/or dimethyl $C_{11}$–$C_{13}$ straight chain alkyl amine oxide(s) with the perfumed oil to form an amine oxide-perfume oil premix; admixing the amine oxide-perfumed oil premix with an aqueous alkali metal hypochlorite solution, and combining an alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12–13.5 and then combining the resulting aqueous hypochlorite solution with the aforementioned premix. The resulting composition is indicated to cause products to which said composition is applied to have eliminated therefrom the disagreeable characteristics "hypochlorite" aroma and instead to have a "clean fresh" or "floral" or "woody" or "citrusy" aroma to be imparted to the treated products. In addition, it is stated that the hands of the individual user after using and being in direct contact with the hypochlorite composition will not have the disagreeable characteristics "hypochlorite" aroma but instead will have a plesant "clean fresh" or "floral" or "woody" or "citrusy" aroma.

The disadvantage of the system of U.S. Pat. No. 3,876,551, however, concerns (a) the inability to use a thickener in the system whereby the resulting liquid has a viscosity of 5–25 centiposes at 20°–40° C. and (b) the relative chemical stability and substantive stability of the perfume oil and of the single liquid phase system. Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the system taught in the prior art.

Furthermore, nothing in the prior art including the teaching of U.S. Pat. No. 3,876,551 states either explictly or implicitly the compatability of a thickener in the instant system, such as sodium palmitate, sodium stearate, potassium, palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

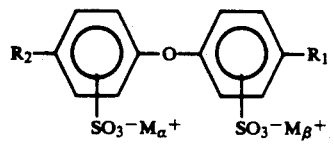

(wherein $R_1$, $R_2$, $M$ and $M_\beta$ are defined, supra) with perfume and hypochlorite bleach in general, is set forth in the Kao Soap Company, Japanese Patent No. 25514/79 filed on Nov. 2, 1973 and opened for public inspection on Jun. 19, 1975. Thus, on page 2, at column 4, line 15, the compound:

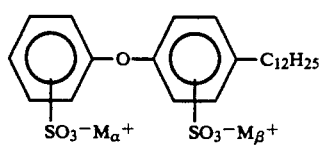

is disclosed for use in conjunction with the perfumed hypochlorite bleaches. The claim of the Kao Soap Patent is as follows:

"Claim: An aromatic liquid bleaching composition containing, as active ingredient, sodium, hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylarbinyl acetate, dihydroterpinyl sacetate, diphenyl oxide, dimethylbenzyl carbinol, dimethylphenyl, carbinol dihydroterpineol, fenchyl acetate, fenchyl alcohol, p-methyldimethylbenzylcarbinol, methylphenylcarbinyl acetate, methyl-n-valerate, muskmoskene, muscarone, methylamyl keton, phenylethyldimethylcarbinyl acetate, rose phenone, styrallyl propionate, tetra-hydromuguol, tetra-hydromuguyl acetate, tertra-hydrolinallol, tetrahydrolinalyl acetate, verool, veleton, verdox, coniferan and yarayara, and a surface solution of sodium hypochlorte."

Furthermore, the use of such compounds as those having the structure:

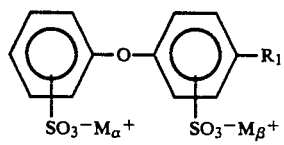

(wherein $R_1$, $R_2M$ and $M_\beta$ have been previously defined) with the hypochlorite bleaches is documented in the brochure of Dow Chemical entitled "DOWFAX ® Surfactants" and is covered in the Dow Chemical Company U.S. Pat. No. 3,172,861 issued on Mar. 9, 1965.

The 2,2-dimethyl-4(2' or 4'-pyridyl) butyronitriles of our invention are unique insofar as the aforementioned system are concerned for use in hypochlorite bleaches. Nothing in the prior art discloses organic compounds having a structure like any of the 2,2-dimethyl-4(2' or 4'-pyridyl) butyronitriles of our invention for use as stable aroma imparting, augmenting or enhancing agents in hypochlorite bleaches.

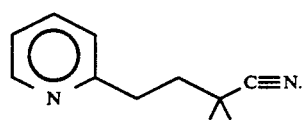

Figure 2:
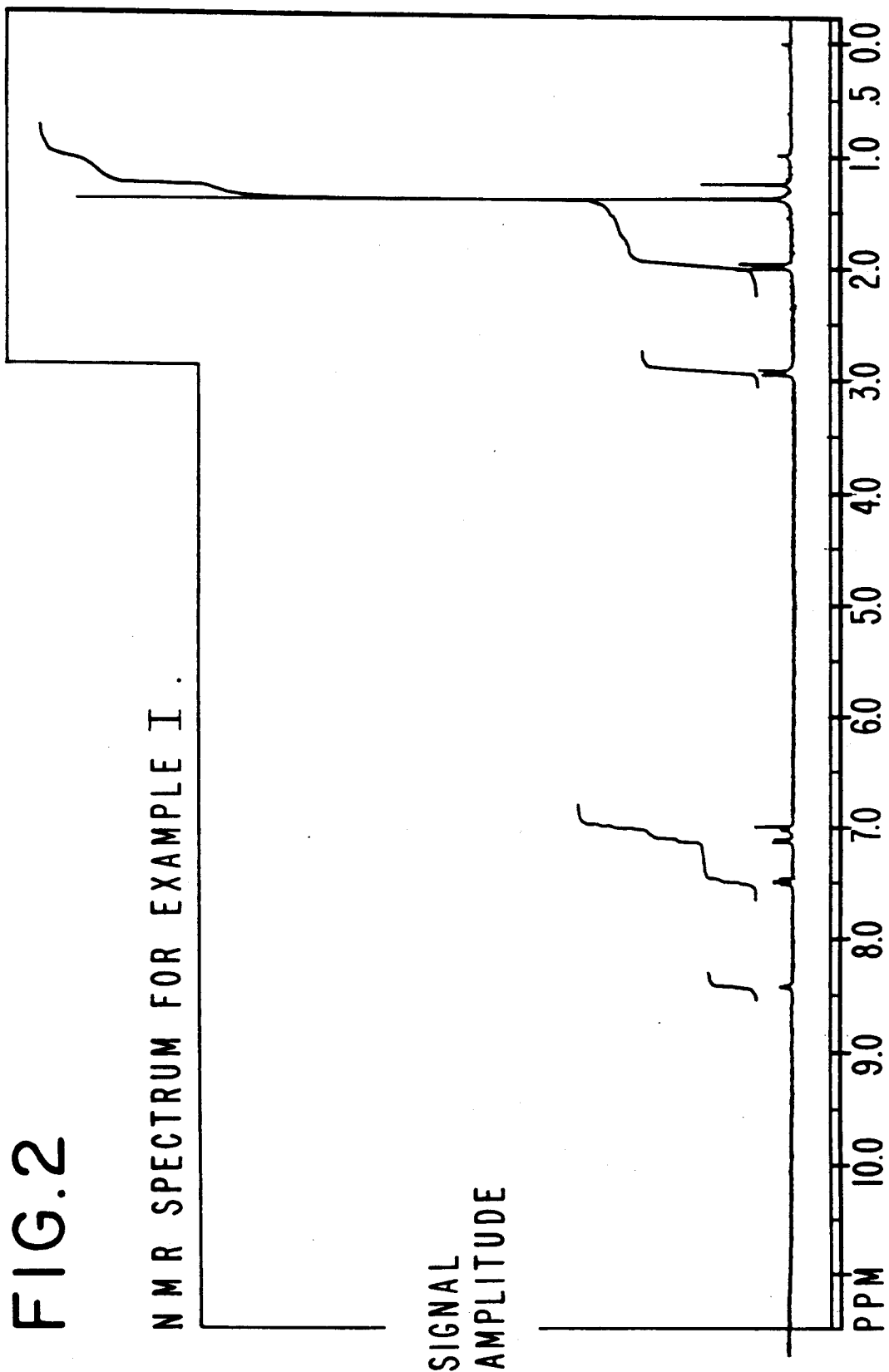

FIG. 2 is the NMR spectrum for the compound having the structure:

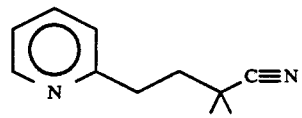

prepared according to Example I.

Figure 3:
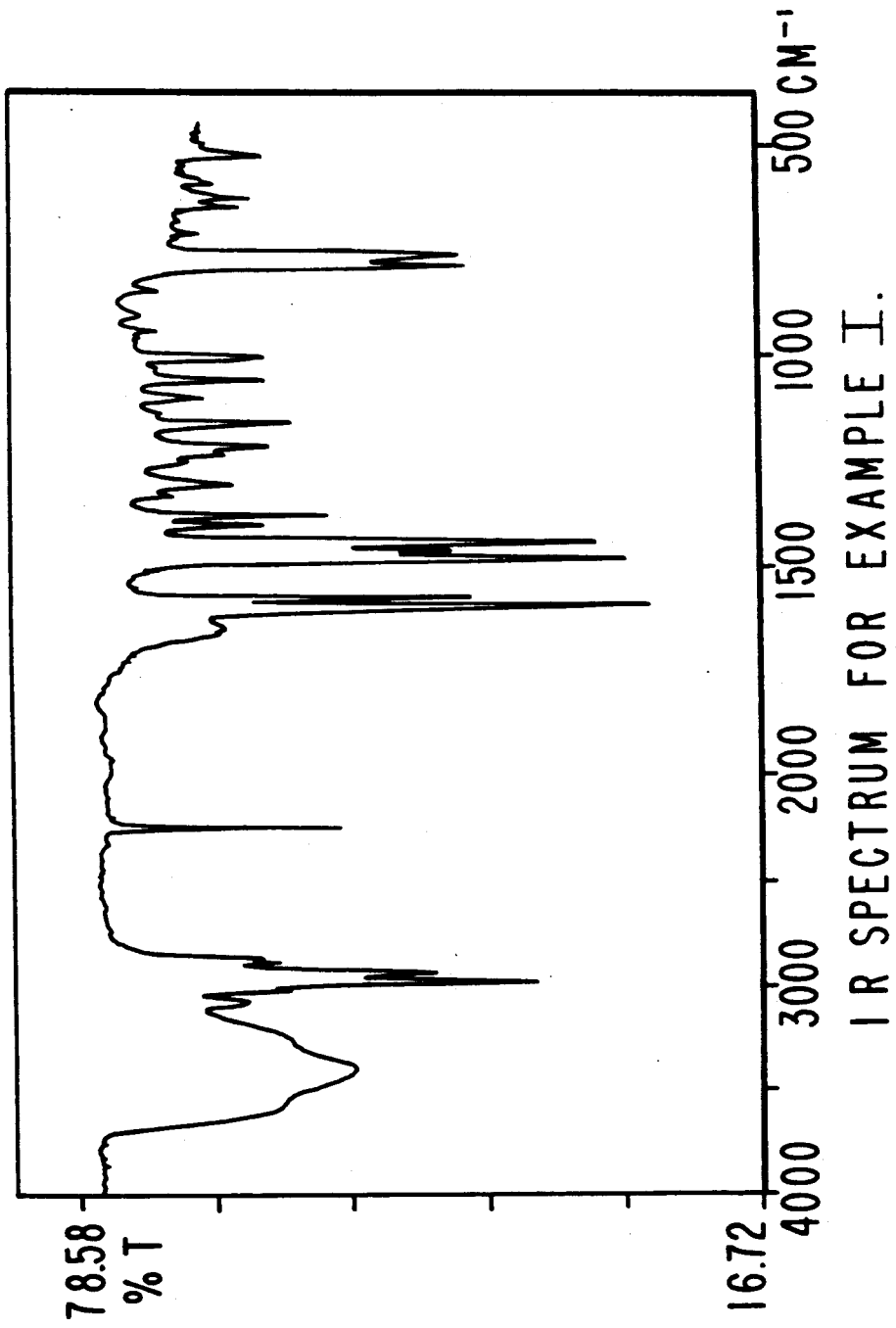

FIG. 3 is the infra-red spectrum for the compound having the structure:

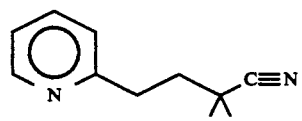

prepared according to Example I.

Figure 4:
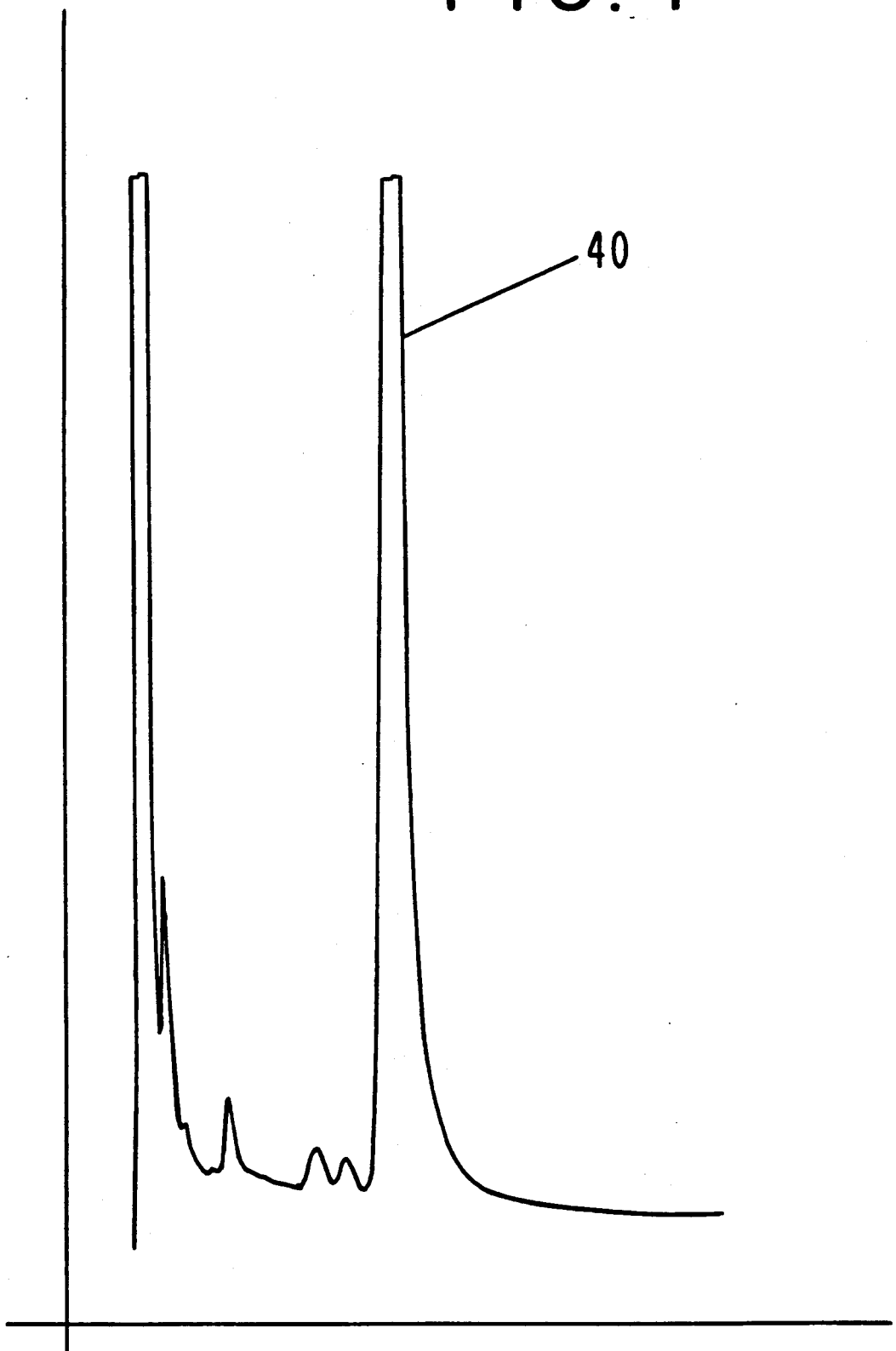

FIG. 4 is the GC spectrum for the reaction product containing the compound having the structure:

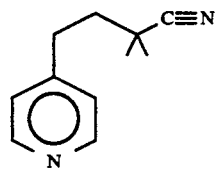

prepared according to Example II (Conditions: SE-30 column programmed at 180° C. isothermal).

Figure 5:
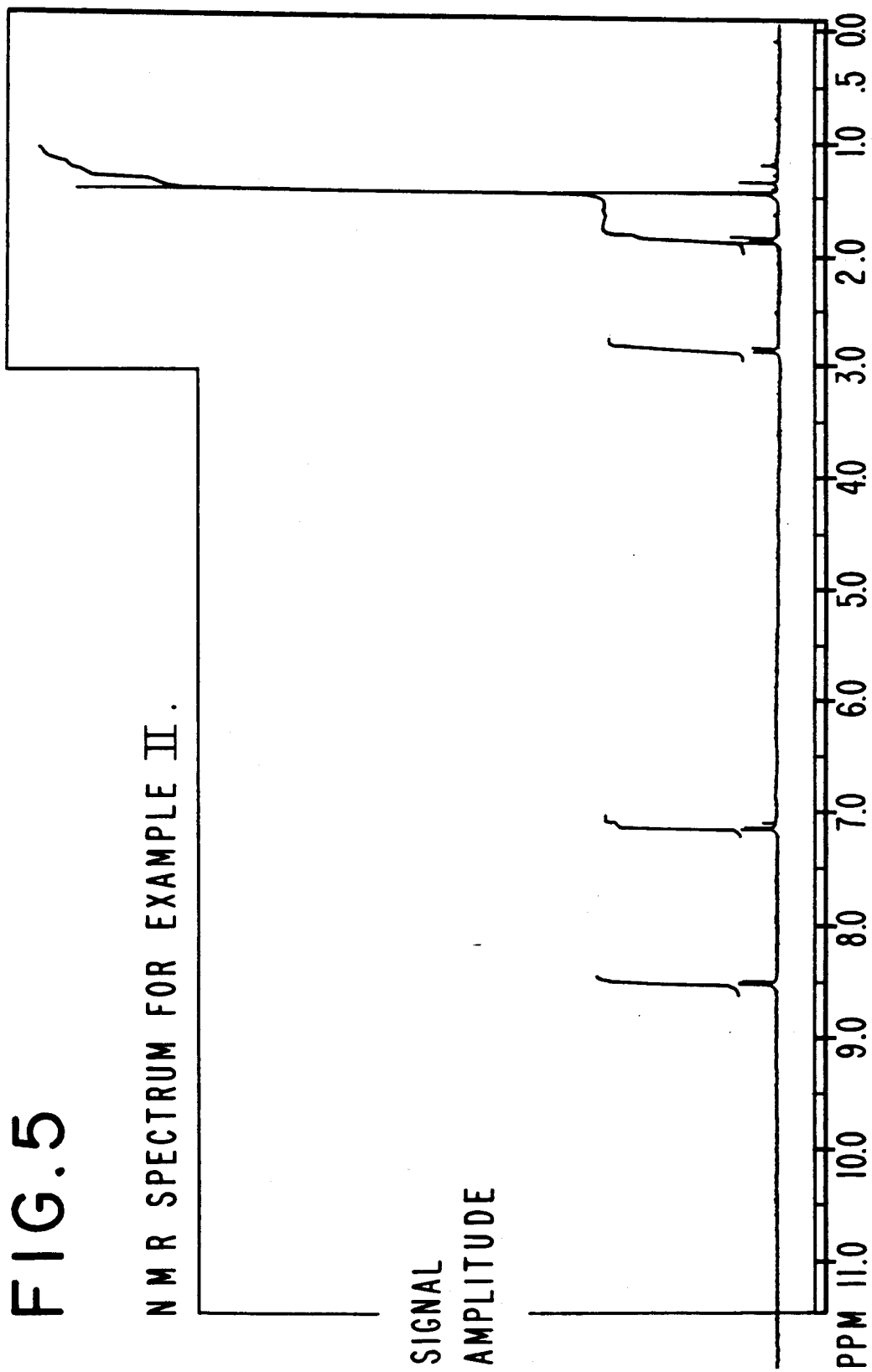

FIG. 5 is the NMR spectrum for the compound having the structure:

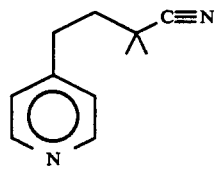

prepared according to Example II.

Figure 6:
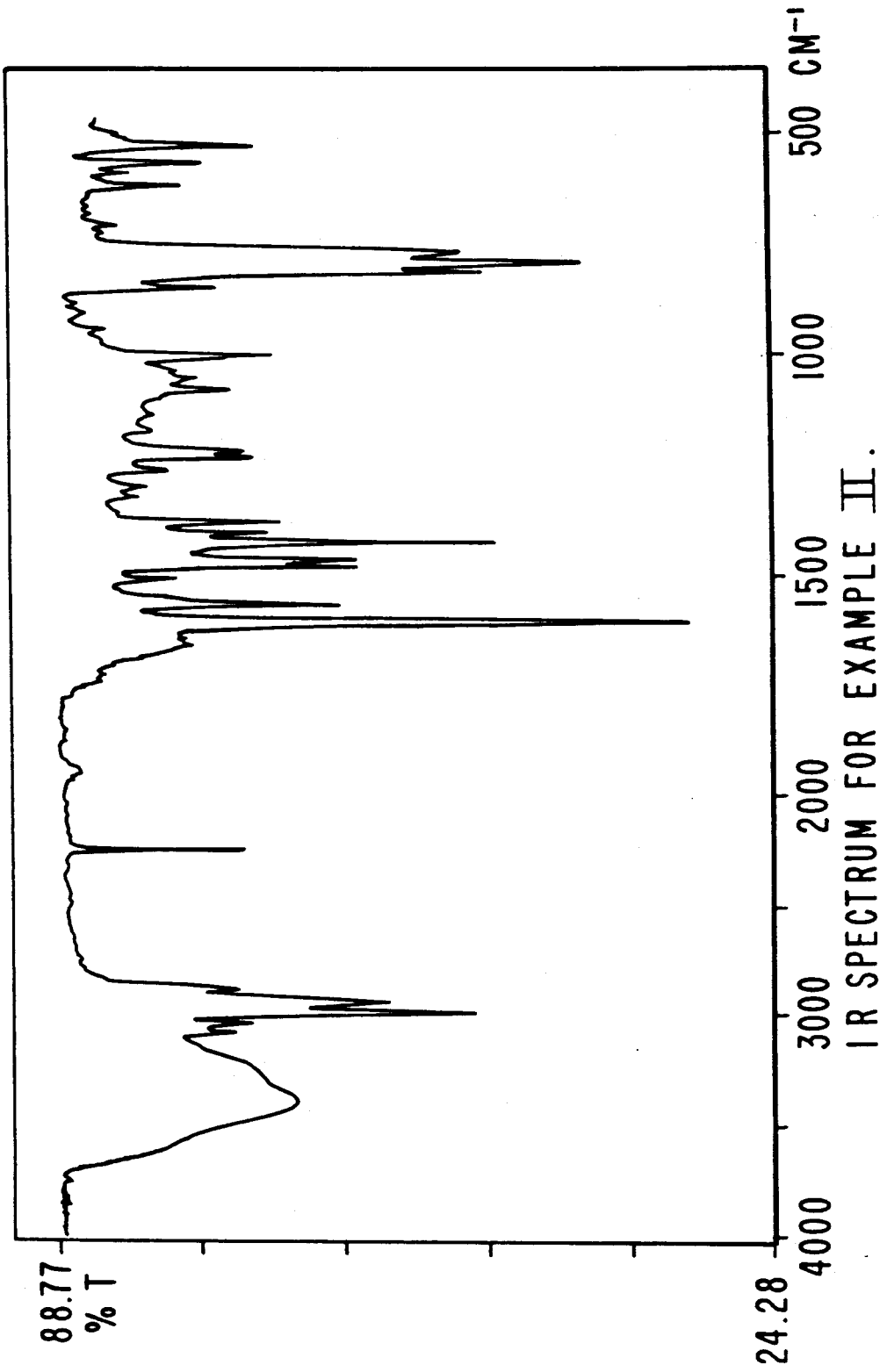

FIG. 6 is the infra-red spectrum for the compound having the structure:

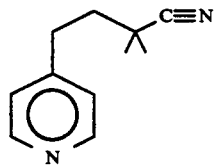

prepared according to Example II.

Figures 7, 8:
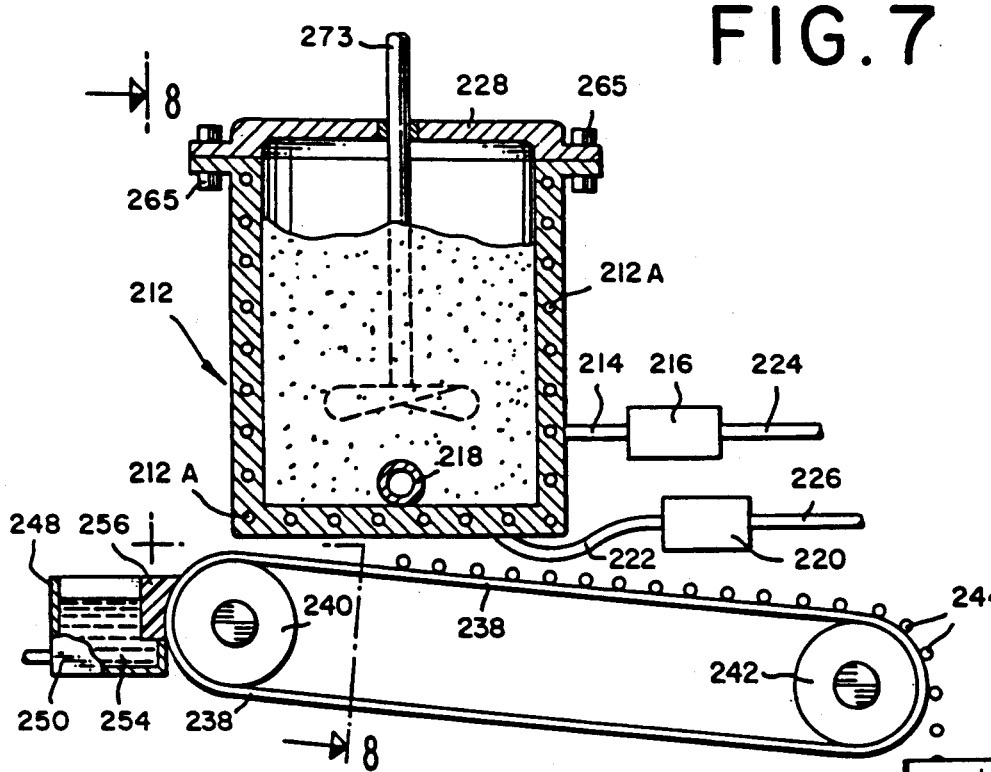

FIG. 7 represents a cut-away side elevation view of apparatus used in forming perfumed polymers which contain imbedded therein one of the 2,2-dimethyl-4(2' or 4'-pyridyl) butyronitriles of our invention.

FIG. 8 is a front view of the apparatus of FIG. 7 looking in the direction of the arrows.

DETAILED DESCRIPTION OF THE DRAWINGS

Figure 1:
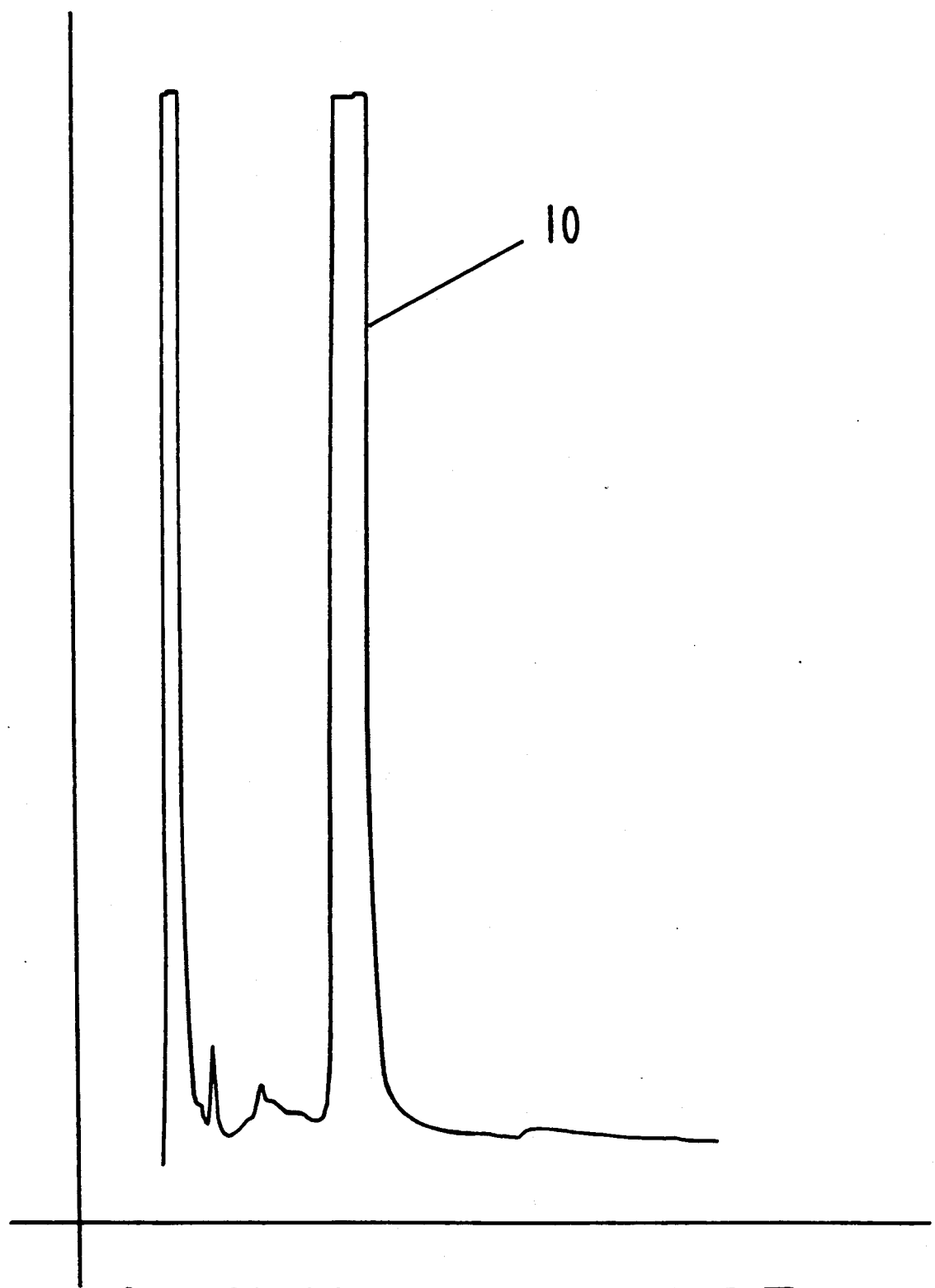
FIG. 1 is the GC spectrum for the reaction product of Example I containing the compound having the structure.

FIG. 1 is the GC spectrum for the reaction product of Example I. The peak indicated by reference numeral 10 is the peak for the compound having the structure:

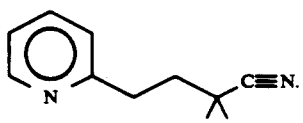

FIG. 4 is the GC spectrum for the reaction product of Example II. The peak indicated by reference numeral 40 is the peak for the compound having the structure:

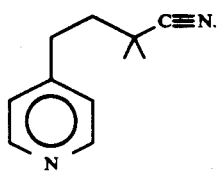

Referring to FIGS. 7 and 8 there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 7 and 8, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the 2,2-dimethyl-4(2' or 4'-pyridyl) butyronitriles of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220-270 C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition of perfume material which contains at least one of the 2,2-dimethyl-4(2' or 4'-pyridyl) butyronitriles of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with at least one of the 2,2-dimethyl-4(2' or 4'-pyridyl) butyronitriles of our invention and one or more other substances, will continuously drop through the orifices 234 downwardly from the conduit 232. During this time, the temperature of the polymer intimately admixed with the perfumery substance in the container 212 is accurately controlled so that a temperature in a range of from about 240°-250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is all of or which contains one of the 2,2-dimethyl-4(2' or 4'-pyridyl) butyronitriles of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides processes for preparing 2,2-dimethyl-4(2' or 4'-pyridyl) butyronitriles as well as the use of said 2,2-dimethyl-4(2' or 4'-pyridyl) butyronitriles in augmenting, enhancing or imparting aroma to or in perfume compositions, perfumed articles and colognes.

The process for preparing the 2,2-dimethyl-4(2' or 4'-pyridyl) butyronitriles encompasses the reactions:

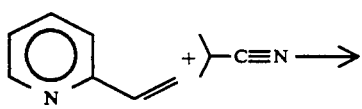

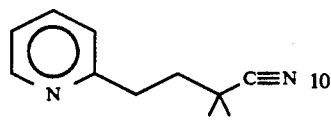

and

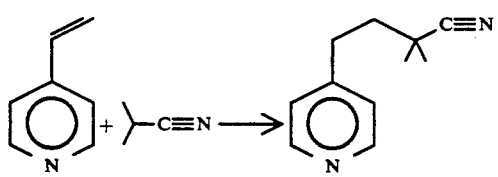

shown generically by the reaction:

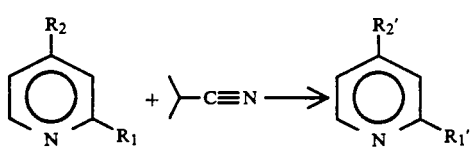

wherein one of the moieties $R_1$ or $R_2$ is vinyl having the structure:

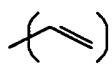

and the other of $R_1$ or $R_2$ is hydrogen; and wherein one of the moieties $R_1'$ and $R_2'$ has the structure:

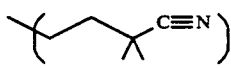

and the other of $R_1'$ and $R_2'$ is hydrogen. The resulting compounds having the structures:

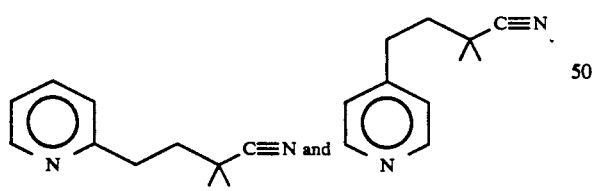

have uses in augmenting or enhancing the aroma of perfume compositions, colognes and perfumed articles including but not limited to perfumed polymers, cosmetic powders, anionic, cationic, nonionic or zwitterionic detergents, fabric softener compositions, fabric softener articles including drier-added fabric softener articles (e.g., BOUNCE ® marketed by the Procter & Gamble Company of Cincinnati, Ohio).

The 2,2-dimethyl-4(2' or 4'-pyridyl) butyronitriles of our invention are capable of imparting, augmenting or enchancing green, new mown hey, fresh lilac, minty and herbaceous aromas with minty and new mown hey undertones to perfume compositions, colognes and perfumed articles including soaps, bleaches, anionic, cationic, nonionic or zwitterionic detergents, fabric softener articles and other perfumed articles.

The process of our invention involves the reaction of isobutyronitrile having the structure:

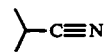

with one of the compounds having the structures:

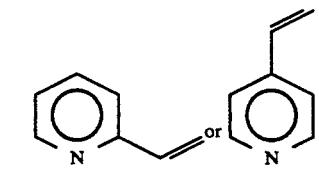

at a temperature in the range of 90°-130° C. in the presence of a catalyst which may either be sodium hydride or lithium diisopropyl amide having the structure:

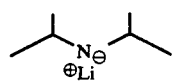

according to the generic reaction:

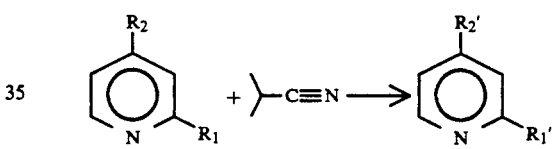

wherein $R_1$ or $R_2$ is vinyl having the structure:

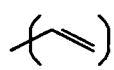

and the other of $R_1$ or $R_2$ is hydrogen; and wherein $R_1'$ or $R_2'$ has the structure:

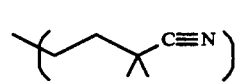

and the other of $R_1'$ or $R_2'$ is hydrogen. Preferably the reaction takes place at atmospheric pressure. The mole ratio of reactants is preferably about 1:1 with an excess of isobutyronitrile (e.g., 50% molar excess) being preferred. The mole percentage of catalyst, e.g., sodium hydride or lithium diisopropyl amide in the reaction may vary from about 5% up to about 20% with the preferred mole percentage range of catalyst varying between 6 and 10%.

The following table sets forth the perfumery properties of the compounds of our invention:

| Structure of Nitrile | Perfumery Properties |
|---|---|
| The compound having the structure: | A green, herbaceous, new mown hey and fresh lilac aroma with minty |

| Structure of Nitrile | Perfumery Properties |
|---|---|
| [pyridine ring with -CH2-CH(CH3)-C≡N side chain, N in ring]<br>prepared according to Example I,<br>(bulked distillation fractions 2 and 3.<br>The compound having the structure: | undertones. |
| [pyridine ring with -CH2-CH(CH3)-C≡N side chain, N in ring]<br>prepared according to Example II, distillation fraction 2. | A minty, herbaceous aroma new mown hey undertones. |

The 2,2-dimethyl-4(2' or 4'-pyridyl) butyronitriles of our invention and one or more auxiliary perfume ingredients, including, for example, hydrocarbons, alcohols, ketones, aldehydes, nitriles (other than the nitriles of our invention), esters, lactones, ethers, hydrocarbons, synthetic essential oils and natural essential oils may be admixed so that the combined odors of the individual components produce a pleasant and desired fragrance particularly and preferably in the "pine fragrance" area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the 2,2-dimethyl-4(2' or 4'-pyridyl) butyronitriles of our invention can be used to alter, modify or enhance the aroma characteristics of a perfume composition, for example, by utilizing or moderating the olfactory reaction contributed by another ingredient in the composition.

The amount of at least one of the 2,2-dimethyl-4(2' or 4'-pyridyl) butyronitriles of our invention which will be effective in perfume compositions as well as in perfumed articles and colognes depends on many factors, including the other ingredients, their amounts and the effects which are desired. It has been found that perfume compositions containing as little as 0.05% of at least one of the 2,2-dimethyl-4(2' or 4'-pyridyl) butyronitriles of our invention can be used impart green, new mown hey, fresh lilac, minty and herbaceous aromas with minty and new mown hey undertones to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effects desired on the finished product and the particular fragrance sought.

At least one of the 2,2-dimethyl-4(2' or 4'-pyridyl) butyronitriles of our invention is useful (taken alone or together with other ingredients in perfume compositions), in detergents and soaps, space odorants and deodorants, perfumes, colognes, toilet water, bath preparations such as lacquers, brillianties, pomades and shampoos, cosmetic preparations such as creams, deodorants, hand lotions and sun screens; powders, such as talcs, dusting powders, face powders and the like.

As little as 0.7% of at least one of the 2,2-dimethyl-4(2' or 4'-pyridyl) butyronitriles of our invention will suffice to impart an intense and substantive green, new mown hey, fresh lilac, minty and herbaceous aroma with minty and new mown hey undertones to pine perfume formulations. Generally, no more than 5% of at least one of the 2,2-dimethyl-4(2' or 4'-pyridyl) butyronitriles of our invention based on the ultimate end product is required to be used "as is" or in the perfume composition.

Furthermore, as little as 0.25% of at least one of the 2,2-dimethyl-4(2' or 4'-pyridyl) butyronitriles of our invention will suffice to impart such aroma to perfumed articles per se, whether in the presence of other perfume materials or whether used by themselves. Thus, the range of use of at least one of the 2,2-dimethyl-4(2' or 4'-pyridyl) butyronitriles of our invention in perfumed articles may vary from about 0.25% up to about 5% by weight based on the total weight of the perfumed article.

In addition, the perfume composition or fragrance compositions of our invention can contain a vehicle or carrier for at least one of the 2,2-dimethyl-4(2' or 4'-pyridyl) butyronitriles of our invention. The vehicle can be a liquid such as a non-toxic alcohol, e.g., ethanol, a non-toxic glycol, e.g., propylene glycol or the like. The carrier can also be an absorbent solid, such as gum (e.g., gum arabic), or components for encapsulating the composition as by means of coacervation (using a gelatin coacervation agent).

It will thus be apparent that the 2,2-dimethyl-4(2' or 4'-pyridyl) butyronitriles of our invention can be utilized to alter, modify or enhance the aroma of perfume compositions, colognes or perfumed articles.

Furthermore, several processes may be used in order to produce a thickened, highly viscous hypochlorite bleaching or sterilizing solution whereby the desired aroma profiles are imparted to the articles treated with said hypochlorite solution.

Thus, for example, one of the 2,2-dimethyl-4(2' or 4'-pyridyl) butyronitriles of our invention may be premixed with the diphenyl oxide derivative or diphenyl oxide derivative-amine oxide solubilizer-stabilizer (having the structures, respectively):

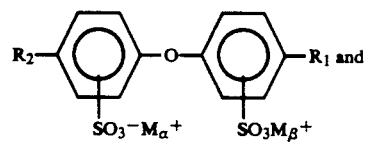

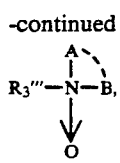

and the resulting 2,2-dimethyl-4(2' or 4'-pyridyl) butyronitrile-containing premix is then mixed with the hypochlorite bleaching or sterilizing solution with stirring. Immediately after such addition, an aqueous alkali metal hydroxide solution is added to the mixture to bring the pH invention of the system; and (3) will limit the particular ingredients useable in such perfume oils in conjunction with the 2,2-dimethyl-4(2' or 4'-pyridyl) butyronitriles. On the other hand, if for example, the 2,2-dimethyl-4(2' or 4'-pyridyl) butyronitriles is used alone or further in combination with (i) diisoamylene epoxides; (ii) diisoamylenes as described in application for U.S. Pat. Ser. No. 188,576 filed on Oct. 9, 1980; now U.S. Pat. No. 4,303,555 issued on Dec. 1, 1981; or (iii) acyl diisoamylene derivatives described in application for U.S. Pat. Ser. No. 184,132 filed on Sep. 4, 1980, now U.S. Pat. No. 4,321,255 issued on Mar. 23, 1982; and/or (iv) ketal derivatives of acyl diisoamylene derivatives described in application for U.S. Pat. Ser. No. 212,993 filed on Dec. 4, 1980, now U.S. Pat. No. 4,315,952 issued on Feb. 16, 1982, a pH of about 14.0 and even slightly higher (e.g., 14.1) is acceptable.

The aqueous alkali metal hydroxide can be added to the aqueous alkali metal hypochlorite solution before adding the diphenyl oxide derivative (taken alone or in conjunction with the amine oxide) or the 2,2-dimethyl-4(2' or 4'-pyridyl) butyronitriles with other materials such as diisoamylene epoxides. Indeed, the ingredients: the 2,2-dimethyl-4(2' or 4'-pyridyl) butyronitriles; the alkali metal hydroxide and the diphenyl oxide derivative or diphenyl oxide derivative-amine oxide composition (having the structures, respectively:

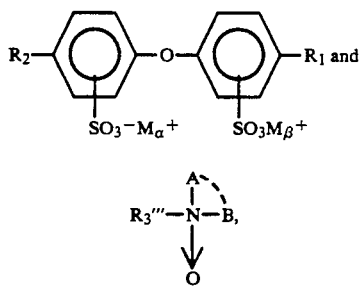

may be added or admixed in any order which is convenient to the formulator.

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydroxide and sodium hydroxide, or, if desired, mixtures of such hydroxides.

The temperature at which the composition of our invention remains both substantially stable and commercially useful for the purposes set forth herein (that is, remains as a clear single aqueous or gel phase) and retains (1) the desired properties inherent in the known bleaching and sterilizing uses of aqueous alkali metal hypochlorite liquid or gel solutions, and (2) the properties imparted thereto as a result of the use of at least one of the 2,2-dimethyl-4(2' or 4'-pyridyl) butyronitriles which impart to articles previously subjected to the aqueous alkali metal hypochlorite gel or liquid solutions a desired aroma profile, varies from approximately 20° F. up to approximately 120° F. at temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$–$C_{12}$ straight chain or branched chain diphenyl oxide alkali metal sulfonate or diphenyl oxide derivative-amine oxide premix; (2) then combine the resulting premix with an alkali metal hypochlorite solution; (3) then add the thickening agent; and then (4) adjust the pH of the resulting solution to the range of 11–14.0, then the temperature of mixing ranges which are considered to be within the scope of this invention are as follows:

| | | |
|---|---|---|
| (a) | formation of the diphenyl oxide derivative or diphenyl oxide-amine oxide-2,2-dimethyl valeronitrile premix | 20° F.–150° F. |
| (b) | mixing the premix with aqueous alkali metal hypochlorite solution followed by thickening agent | 20° F.–120° F. |
| (c) | adjustment of pH of the solution to the range of 11–14.0 using aqueous alkali metal hydroxide solution | 20° F.–120° F. |

In any event, whenever a mixing unit operation involves the aqueous alkali metal hypochlorite solution, the temperature of mixing is limited to the range of 20°–120° F. Where the mixing unit operation involves the giving of one of the 2,2-dimethyl-4(2' or 4'-pyridyl) butyronitriles, the upper bound of the temperature range is limited by the stability of the 2,2-dimethyl-4(2' or 4'-pyridyl) butyronitriles useable in the practice of our invention, and the lower bound of said temperature range is limited by the least temperature where a single liquid phase or gel phase including the 2,2-dimethyl-4(2' or 4'-pyridyl) butyronitriles or other ingredients admixed therewith will exist. Where a unit mixing operation of the process of our invention involves the mixing of one or more diphenyl oxide derivative having the generic structure:

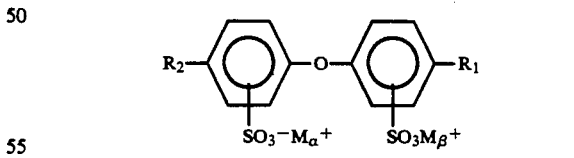

taken alone or taken together with one or more amine oxides having the generic structure:

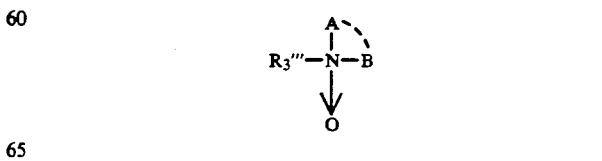

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine oxide mixture will exist.

Preferred diphenyl oxide derivative compositions from a practical standpoint useful in the practice of our invention are compounds having the structure:

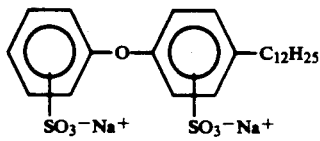

where the $C_{12}-H_{25}$ moiety represents one or a series of different branched chains; compounds defined according to the structure:

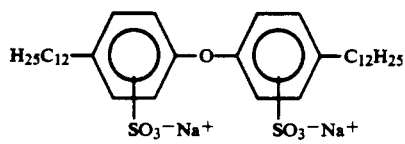

where the $C_{12}H_{25}$ moiety represents one or a series of different branched chains; compounds defined according to the structure:

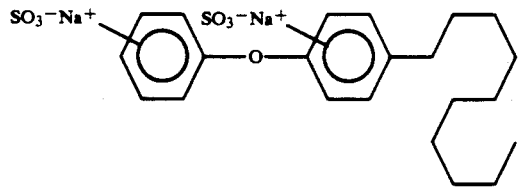

and compounds defined according to the structure:

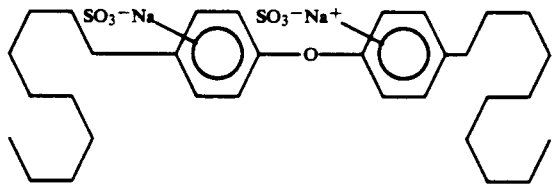

otherwise known as DOWFAX® 2A1 in the case where one of $R_1$ or $R_2$ represents branched $C_{12}H_{25}$alkyl chains and the other of $R_1$ or $R_2$ represents hydrogen, or DOWFAX® 3B2 in the case where one of $R_1$ or $R_2$ represents straight $C_{10}$alkyl chain and the other of $R_1$ or $R_2$ represents hydrogen (DOWFAX® being a registered trademark of the Dow Chemical Company of Midland, Mich.).

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}-C_{16}$ straight chain alkyl amine oxides; more particularly a mixture containing approximately 70% $C_{12}$ straight chain alkyl aines oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}-C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMOX® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Ill. These materials are described in Brochure 68011, published by Armour Industrial Chemicals, P. O. Box 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine oxide of the 2,2-dimethyl-4(2' or 4'-pyridyl) butyronitriles covered by our invention. The usual percent of alkali metal hypochlorite in solution is about 5%, t of sodium hypochlorite in such mixtures as CLOROX® the registered trademark of the Clorox Corporation.

The perfume oil used in conjunction with the 2,2-dimethyl-4(2' or 4'-pyridyl) butyronitriles which, in turn, is used in conjunction with the aqueous alkali metal hypochlorite solution must have such properties as to be able (1) to be compatible with the 2,2-dimethyl-4(2' or 4'-pyridyl) butyronitriles; (2) to impart to the resulting or "aqueous alkali metal hypochlorite" liquid or gel solution a pleasant aroma which is harmonizes with the aroma of the 2,2-dimethyl-4(2' or 4'-pyridyl) butyronitriles; (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long-lasting stable aroma. Examples of ingredients compatible with 2,2-dimethyl-4(2' or 4'-pyridyl) butyronitriles and suitable for the aforementioned purposes, that is, useable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. Nos. 3,360,530 and 3,591,528 such as 6-oxa-1,1,3,3,8-pentamethyl-2-3,5,6,7,8-hexahydro-1H-benz(1)indene;
3. Polycyclic ethers covered by U.S. Pat. No. 3,281,432 such as octahydro-1,3a,6-trimethyl-1H-1,6a, ethanopentaleno-(1,2-C)Furan;
4. Polycyclic ketones such as hexahydro-1,1,5,5-tetramethyl-2H-2,4a-methanonaphthalen-8-(5H)one;
5. Diisoamylenes described according to application for U.S. Pat. Ser. No. 188,576 filed on Sep. 18, 1980;
6. Acyl diisoamylene derivatives described according to application for U.S. Pat. Ser. No. 184,132 filed on Sep. 4, 1980 and ketal derivatives thereof described according to application for U.S. Pat. Ser. No. 212,993 filed on Dec. 4, 1980; and
7. Diisoamylene epoxide derivatives prepared according to application for U.S. Pat. Ser. No. 231,773 filed on Feb. 27, 1981.

It will be understood that a number of materials which impart to the green, new mown hey, fresh lilac, minty and herbaceous aroma with minty and new mown hey undertones to pine perfume formulations of our invention additional eucalyptol or minty or woody nuances will not be useful for this aspect of our invention because they are, inter alia, easily oxidized by the alkali metla hypochlorite in the system. Examples are 1,5.9-trimethyl-12,acetyl-cyclodlodecatriene-1,5,8 and 1,5,9-trimethyl-12-cyclododecadien covered by British Patent No. 1,204,409.

A basic feature of our invention concerns the fact that the only detergent group needed or desirable in the composition of our invention is the class of diphenyl oxide derivatives defined according to the structure:

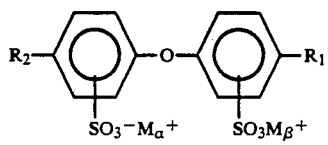

wherein $R_1$, $R_2$ M and $M_\beta$ are defined, supra, taken alone or in combination with the class of morpholino and/or dimethyl $C_{11}$–$C_{13}$ straight chain alkyl amine oxides defined according to the structure:

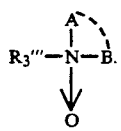

More specifically, such detergents as sodium decyl ether sulfate, sodium myristyl ether sulfate, sodium lauryl ether sulfate and lithium lauryl ether sulfate are neither desired nor are they required. Furthermore, the well known hydrotropes employed in prior art compositions such as the well known family of clarifying agents comprising the alkali metal or alkali earth metal salts of mono-and polyalkylated benzene or naphthalene sulfonates such as sodium xylene or magnesium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system; hypochlorite bleach-2,2-dimethylk-4-phenyl valeronitrile-diphenyl oxide derivative or diphenyl oxide derivative-amine oxide derivative (having the general structure:

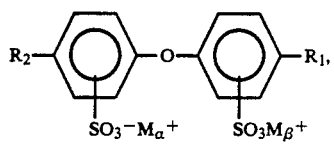

and having the structure:

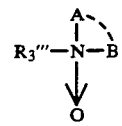

of our invention).

Still another basic feature of our invention concerns the fact that the gel phase compositions including thickener agents are employed with the "premix" system: 2,2-dimethyl-4-phenyl valeronitrile-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being in a semi-solid state, is unobviously, advantageously and unexpectedly stable over long periods of time. Percentages of thickening agents such as sodium palmitate, sodium stearate, sodium laurate, potassium palmistate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide derivative (or diphenyl oxide derivative-amine oxide)-2,2-dimethyl-4-phenyl valeronitrile composition of our invention. When it is merely desired to have a thickened "premix" the percentage of thickening agent may vary from about 5% up to about 40% by weight of thickener based on overall weight of "premix".

The following Examples I and II serve to illustrate processes of our invention. Examples following Example II serve to illustrate specific embodiments of our invention. It will be understood that these examples are illustrative and that the invention is to be considered restricted thereto only as indicated in the appended claims.

All parts and percentages given herewith are by weight unless otherwise specified.

EXAMPLE I

Preparation of 2,2-Dimethyl-4(2'-Pyridyl)Butyronitrile

Reaction:

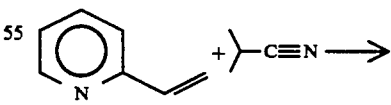

Into a 2 liter reaction flask equipped with stirrer, thermometer, reflux condenser and heating mantle is placed 35 grams of sodium hydride. 640 Grams (9.28 moles) of isobutylnitrile having the structure:

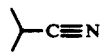

is then added to the sodium hydride thereby forming a suspension. The resulting suspension is then heated to 95° C. Over a period of two hours while maintaining the temperature under 100° C., 488 grams (4.64 moles) of 2-vinyl pyridene having the structure:

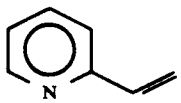

is added to the reaction mass. The reaction mass is heated with stirring for a period of 1.5 hours at 95° C.

The reaction mass is then cooled to 30° C.

500 ml Water is then added dropwise to the reaction mass. Then, in sequence:
500 ml toluene;
1000 ml water; and
125 ml acetic acid
is added to the reaction mass causing the pH to be 7. The reaction mass is then stirred for 0.5 hours and the organic phase separates from the aqueous phase. The aqueous phase is extracted with 300 ml toluene. The toluene extract is combined with the organic phase. The resulting product is then washed with 500 ml saturated sodium chloride. The resulting product is then washed with 500 ml saturated sodium chloride. The resulting product is then filtered through anhydrous magnesium sulfate and distilled to yield 609 grams of product. The distillation yields the following fractions:

| Fraction No. | Vapor Temp. (°C.) | Liquid Temp. (°C.) | Vacuum mm/Hg. Pressure |
|---|---|---|---|
| 1 | 47/46 | 52/84 | 100/1.99 |
| 2 | 102 | 112 | 1.55 |
| 3 | 110 | 124 | 2.32 |
| 4 | 94 | 134 | 2.32. |

Fractions 2 and 3 are bulked. Bulked distillation fractions 2 and 3 have a green, herbaceous, new mown hey and fresh lilac aroma with minty undertones.

The compound having the structure:

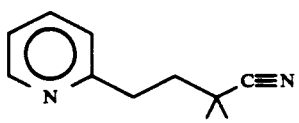

is confirmed to be that which is fractions 2 and 3 by NMR and IR analyses the spectra for which are set forth in FIGS. 2 and 3 described, supra.

EXAMPLE II

Preparation of 2,2-Dimethyl-4(4'-Pyridyl)Butyronitrile

Reaction:

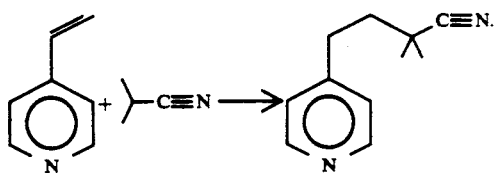

Into a 5 liter reaction flask equipped with stirrer, thermometer, reflux condenser, heating mantle and addition funnel is placed 35 grams (1.16 moles) of sodium hydride. With stirring while maintaining the reaction mass at 27° C., 640 grams of isobutylnitrile having the structure:

is added to the reaction mass. The reaction mass is then heated to 80° C. and maintained at 80° C. for a period of two hours. The reaction mass is then heated to 95° C. and while maintaining the reaction mass at 95°-100° C., over a two hour period, 488 grams (4.64 moles) of 4-vinyl pyridine having the structure:

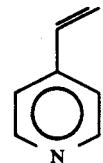

is added to the reaction mass. The reaction mass is then maintained at 94°-95° C. for a period of 1.4 hours. At the end of the 1.4 hour period, the reaction mass is cooled to 35° C.

500 ml Water is added dropwise; followed by 500 ml toluene. 325 ml Acetic acid is then added to the reaction mass in order to break up the resulting emulsion. The pH of the reaction mass is now 8. The resulting product is cooled to 30° C. and the organic phase is separated from the aqueous phase. The aqueous phase is extracted with 300 ml toluene. The toluene extract is combined with the organic phase. The resulting product is washed with 500 ml saturated sodium chlorite to bring pH to 7. The resulting product is then filtered through anhydrous magnesium sulfate and distilled to yield the following fractions:

| Fraction No. | Vapor Temp. (°C.) | Liquid Temp. (°C.) | Vacuum mm/Hg. Pressure |
|---|---|---|---|
| 1 | 47/88 | 47/52 | 1.15/1.25 |
| 2 | 123 | 134 | 2.48 |
| 3 | 108 | 200 | 1.45. |

Fraction 2 has the structure:

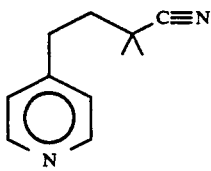

and this product has a minty and herbaceous aroma with new mown hey undertones. The compound having the structure:

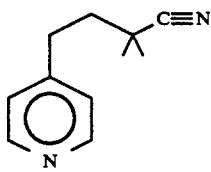

has its structure confirmed by NMR and IR analysis as is set forth in FIGS. 5 and 6 described, supra.

EXAMPLE III

The following Chypre formulations are prepared:

| Ingredients | Parts by Weight III(A) | III(B) |
|---|---|---|
| Musk aambrette | 40 | 40 |
| Musk ketone | 60 | 60 |
| Coumarin | 30 | 30 |
| Oil of bergamot | 150 | 150 |
| Oil of lemon | 100 | 100 |
| Methyl ionone | 50 | 50 |
| Hexyl cinnamic aldehyde | 100 | 100 |
| Hydroxycitronellal | 100 | 100 |
| Oil of lavender | 50 | 50 |
| Texas cedarwood oil | 85 | 85 |
| Virginia cedarwood oil | 30 | 30 |
| Oil of sandalwood (East Indies) | 40 | 40 |
| Eugenol | 10 | 10 |
| Benzyl acetate | 30 | 30 |
| alpha-Phenyl ethyl alcohol | 40 | 40 |
| beta-Phenyl ethyl alcohol | 30 | 30 |
| Oakmoss absolute | 30 | 30 |
| Vetiver oil Venezuela | 25 | 25 |
| The compound having the structure: 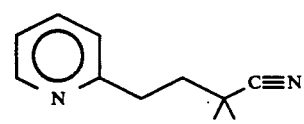 | 72 | 0 |
| The compound having the structure: 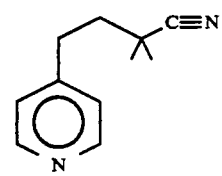 | 0 | 72 |

The compound having the structure:

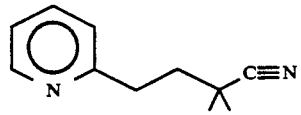

imparts to this Chypre formulation green, herbaceous, new mown hey, fresh lilac and minty undertones. Accordingly, the formulation of Example III(A) can be described as "a Chypre aroma with green, herbaceous, new mown hey, fresh lilac and minty undertones".

The compound having the structure:

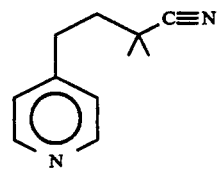

imparts to this Chypre formulation minty, herbaceous and new mown hey undertones. Accordingly, the formulation of Example III(B) can be described as "a Chypre aroma with minty, herbaceous and new mown hey undertones".

EXAMPLE IV

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: (pyridine compound) prepared according to Example I, bulked distillation fractions 2 and 3. | A green, herbaceous, new mown hey and fresh lilac aroma with minty undertones. |
| The compound having the structure: (pyridine compound) prepared according to Example II, distillation fraction 2. | A minty and herbaceous aroma with new mown hey undertones. |
| Perfume composition of Example III(A). | A Chypre aroma with green, herbaceous, new mown hey, fresh lilac and minty undertones. |
| Perfume composition of Example III(B). | A Chypre aroma with minty, herbaceous and new mown hey undertones. |

EXAMPLE V

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentration of substance as set forth in Table II of Example IV.

EXAMPLE VI

Preparation of Colognes and Handkerchief Perfumes

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

Preparation of Soap Compositions

One hundred grams of soap chips [per sample] IVORY ®, produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example IV.

EXAMPLE VIII

Preparation of Solid Detergent Compositions

Detergents are prepared using the following ingredients according to Example I of Canadian Patent No. 1,007,948:

| Ingredient | Percent by Weight |
|---|---|
| "NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20-22}$HAPS
   22%—isopropyl alcohol
   20%—antistatic agent
   1%—of one of the substances as set forth in Table II of Example IV.

EXAMPLE X

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol, 8.0 grams of the polymer is dissolved in the alcohol. The following ingredients are added to the PVP/VA alcoholic solution.

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.10 |
| One of the perfumery substances as set forth in TABLE II of Example IV. | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled at 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

EXAMPLE XII

Four drops of each of the substances set forth in Table II of Example IV, supra, is added separately to two grams of AROMOX® DMC-W to produce a clear premix. The clear premix is added to 200 grams of CLOROX® with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example IV. Furthermore, no such characteristic "hypochlorite" aroma is retained on the hands of the individual handling such laundry in both the wet and the dry states.

EXAMPLE XIII

AROMOX® DMMC-W in various quantities is mixed with 0.1 grams of one of the substances as set forth in Table II of Example IV, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX® DMMC-W | Clarity of Hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% of relative humidity, yields substantially no characteristic "hypochlorite" odor, but does have a faint, pleasant aroma as set forth in Table II of Example IV. Furthermore, no such characteristic "hypochlorite" aroma is retainted on the hands of the individual handling such laundry in both the wet and the dry states.

EXAMPLE XIV

Two grams of AROMOX® DMMC-W is admixed with eight drops of one of the substances set forth in Table II of Example IV, supra. The premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry, on dry-out in an atmosphere of 50% relative humidity retains a "clean" warm aroma as set forth in Table II of Example IV, supra; whereas without the use of the substance set forth in Table II of Example IV, supra, the bleached laundry has a faint characteristic disagreeable "hypochlorite" aroma.

EXAMPLE XV

Two grams of AROMOX® DMMC-W is admixed with eight drops of one of the substances of Table II of Example IV, supra. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table II of Example IV, supra; whereas without the use of the substance set forth in Table II of Example IV, supra, the bleached laundry has a faint characteristic disagreeable "hypochlorite" aroma.

EXAMPLE XVI

Two grams of AROMOX® DMMC-W is admixed with eight drops of one of the substances as set forth in Table II of Example IV, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table II of Example IV, supra, whereas without the use of the substance set forth in Table II of Example IV, supra, the bleached laundry has a faint characteristic disagreeable "hypochlorite" aroma.

EXAMPLE XVII

Four drops of one of the substances set forth in Table II of Example IV, supra, is added to 1.5 grams of AROMOX® to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodiumn hypochlorite solution is used as a laundry bleach, the resulting laundry on dry-out in an atmosphere of 65% relative humidity yields substantially no characteristic "hypochorite" odor but does have a faint pleasant warm, long-lasting aroma as set forth in Table II of Example IV, supra. Furthermore, no such characteristic "hypochlorite" aroma is retained on the hands of the individual handling such laundry in both the wet and dry states.

EXAMPLE XVIII

Four drops of one of the substances set forth in Table II of Example IV, supra, is added to 1 gram n-undecyl-dimethyl amine oxide to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table II of Example IV, supra. Furthermore, no such characteristic "hypochlorite" aroma is retained on the hands of the individual handling such laundry in both the wet and the dry states.

EXAMPLE XIX

Four drops of one of the substances as set forth in Table II of Example IV, supra, are added to 1 gram of n-dodecyl dimethyl amine oxide to produce a clear-premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table II of Example IV, supra. Furthermore, no such characteristic "hypochlorite" aroma is retained on the hands of the individual handling such laundry in both the wet and dry states.

EXAMPLE XX

One gram of n-tridecyl dimethyl amine oxide is admixed with eight drops of one of the substances as set forth in Table II of Example IV, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains the aroma having the nuances described in Table II of Example IV, supra, whereas without the use of one of the substances of Table II of Example IV, supra, the bleached laundry has a faint characteristic disagreeable "hypochlorite" aroma.

EXAMPLE XXI

Four drops of the compound having the structure:

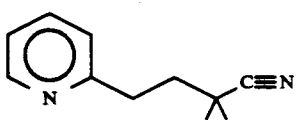

prepared according to Example I (bulked distillation fractions 2 and 3) is added to 2 grams of AROMOX ® DMC-W to produce a clear premix. The clear premix is added to 200 grams of CLOROX ® with stirring resulting in a clear single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a strong fresh substantive green, herbaceous, new mown hey and fresh lilac aroma with minty undertones. Furthermore, no such characteristic "hypchlorite" aroma is retained on the hands of the individual handling such laundry in both the wet and dry states.

EXAMPLE XXII

AROMOX ® DMMC-W in various quantities is mixed with 0.1 grams of the compound having the structure:

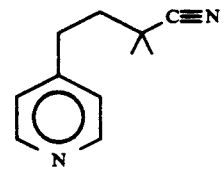

prepared according to Example II, distillation fraction 2. The resulting premix is then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
| --- | --- |
| 0.23% | Clear after three days. |
| 0.15% | Clear after three days. |
| 0.08% | Initially slightly turbid; two phases exist after three days. |

When the 5% aqueous sodium hypochlorite solutions are used as laundry bleaches, the resulting laundry batches on dry-out in an atmosphere of 65% relative humidity yields substantially no characteristic "hypochlorite" odor, but does have a strong fresh, minty and herbaceous aroma with new mown hey undertones.

Furthermore no such characteristic "hypochlorite" aroma is retained on the hands of the individual handling such laundry batches in both the wet and the dry states.

EXAMPLE XXIII

Two grams of AROMOX ® DMMC-W are admixed with eight drops of the compound having the structure:

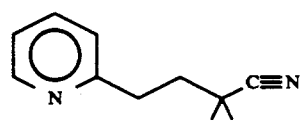

prepared according to Example I (bulked distillation fractions 2 and 3). The premix is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a strong fresh, green, herbaceous, new mown hey and fresh lilac aroma with minty undertones whereas without the use of the compound having the structure:

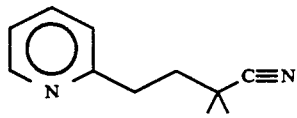

the bleached laundry batches have a faint characteristic disagreeable "hypolchlorite" aroma.

EXAMPLE XXIV

Two grams of AROMOX ® DMMC-W are admixed with eight drops of the compound having the structure:

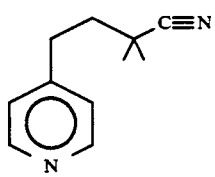

prepared according to Example II (bulked distillation fraction 2). The premix is then added with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a strong fresh minty and herbaceous aroma with new mown hey undertones whereas without the use of the compound having the structure:

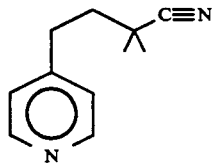

prepared according to Example II the bleached laundry batches have faint characteristic disagreeable "hypochlorite" aromas.

What is claimed is:

1. A process for augmenting or enhancing the aroma of a consumable material selected from the group consisting of perfume compositions, perfumed articles and perfumed polymers comprising the step of intimately admixing with said consumable material an aroma augmenting or enhancing quantity of a compound having a structure selected from the group consisting of:

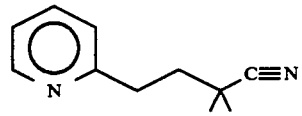

and

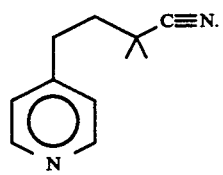

2. A perfume composition comprising a perfume base an intimately therewith an aroma, imparting, augmenting or enhancing quantity of at least one compound having a structure selected from the group consisting of:

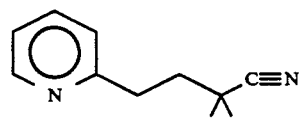

and

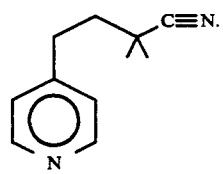

3. A perfumed article comprising a perfumed article base and intimately admixed therewith an aroma, augmenting, enhancing or imparting quantity of at least one compound defined according to the structures:

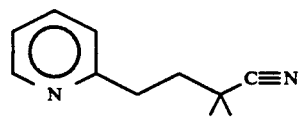

and

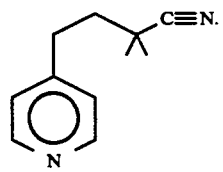

4. A perfumed polymer comprising a microporous polymer and contained within the pores of the microporous polymer an aroma, augmenting, imparting or enhancing quantity of at least one compound defined according the structures:

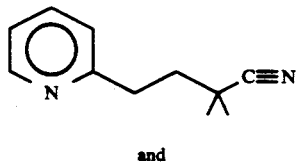

and

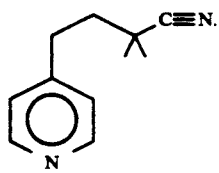

5. A chlorine containing bleach composition comprising:
(a) a chlorine bleach base; and
(b) intimately admixed therewith at least one compound having the structures:

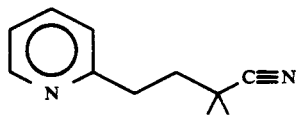

and

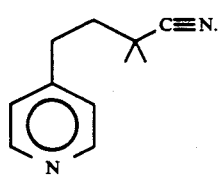

6. A perfumed aqueous alkali metal hypochlorite solution comprising as a sole ingredient the composition of matter selected from the group consisting of (1) at least one substance defined according to the structure:

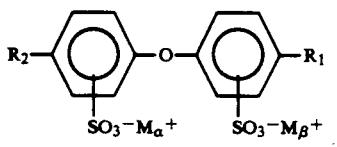

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ and $R_2$ is hydrogen; wherein M and M are the same or different and each represents alkali metal selected from the group consisting of sodium, potassium and lithium and (2) a mixture comprising a material having the structure:

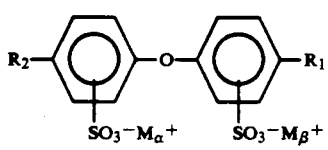

and intimately admixed therewith a substance having the structure:

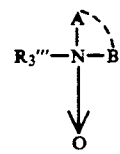

wherein $R_3'''$ is straight chain alkyl; wherein more than 55% of the $R_3'''$ moieties consist of straight chain alkyl having from 11 up to 13 carbon atoms and wherein "A" and "B" are each separately methyl up to 0.2% of one or more compatible perfume oils, said hypochlorite solution having a pH of 11 up to 14.0 and an aroma imparting, augmenting or enhancing quantity of at least one compound having the structure

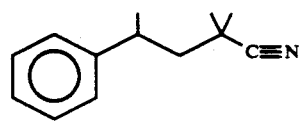

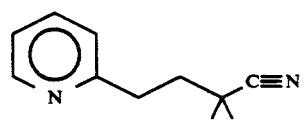

and

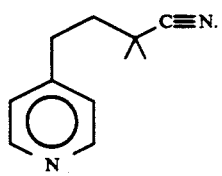

7. A process for producing a 2,2-dimethyl-4(2' or 4'-pyridyl) butyronitriles defined according to the structures:

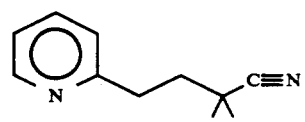

or

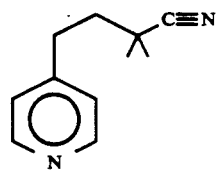

comprising the step of reacting isobutyronitrile having the structure:

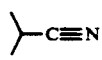

with a compound selected from the group consisting of:

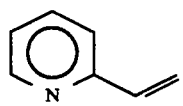
and
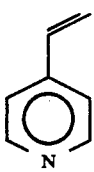
according to the reactions:
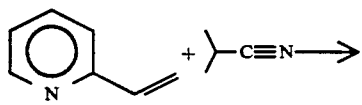
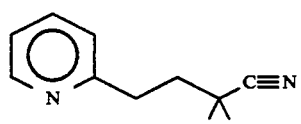
or
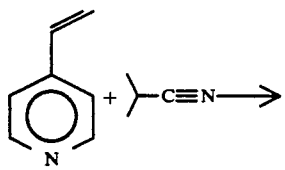
-continued
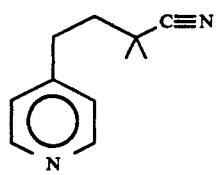
at a temperature in the range of from about 90° C. up to about 130° C. in the presence of a catalyst selected from the group consisting of sodium hydride and lithium diisopropyl amide having the structure:
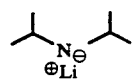
and recovering the resulting reaction product having a structure:
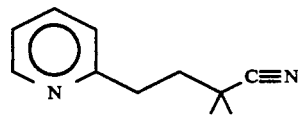
or
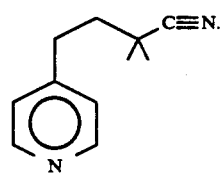
* * * * *